United States Patent
Miyazawa et al.

(10) Patent No.: US 7,759,440 B2
(45) Date of Patent: Jul. 20, 2010

(54) FLUORINE-CONTAINING POLYMERISABLE MONOMER AND POLYMER PREPARED BY USING SAME

(75) Inventors: Satoru Miyazawa, Imafukunakadai (JP); Kazuhiko Maeda, Kandanishikicho (JP); Kenji Tokuhisa, Yamaguchi (JP); Shoji Arai, Yamaguchi (JP)

(73) Assignees: Central Glass Company, Limited, Ube-shi (JP); F-Tech, Inc., Tokyo (JP)

( * ) Notice: Subject to any disclaimer, the term of this patent is extended or adjusted under 35 U.S.C. 154(b) by 972 days.

(21) Appl. No.: 11/485,422

(22) Filed: Jul. 13, 2006

(65) Prior Publication Data
US 2006/0252897 A1 Nov. 9, 2006

Related U.S. Application Data

(62) Division of application No. 10/880,097, filed on Jun. 30, 2004, now Pat. No. 7,094,850, which is a division of application No. 10/198,044, filed on Jul. 19, 2002, now Pat. No. 6,784,312.

(30) Foreign Application Priority Data
Jul. 24, 2001 (JP) ............... 2001-222530

(51) Int. Cl.
*C08F 120/22* (2006.01)
(52) U.S. Cl. ...................... 526/245; 526/246
(58) Field of Classification Search ............... 526/246
See application file for complete search history.

(56) References Cited

U.S. PATENT DOCUMENTS

| | | | | |
|---|---|---|---|---|
| 3,438,946 A | | 4/1969 | Lichstein et al. | |
| 3,544,537 A | * | 12/1970 | Brace | 526/246 |
| 3,781,370 A | * | 12/1973 | Anello et al. | 568/677 |
| 3,920,614 A | * | 11/1975 | Kirimoto et al. | 526/245 |
| 3,944,527 A | * | 3/1976 | McCown | 526/243 |
| 4,578,508 A | | 3/1986 | Griffith et al. | |
| 5,670,593 A | * | 9/1997 | Araki et al. | 526/245 |
| 6,806,026 B2 | * | 10/2004 | Allen et al. | 430/270.1 |
| 2003/0224283 A1 | | 12/2003 | Allen et al. | |

* cited by examiner

*Primary Examiner*—Bernard Lipman
(74) *Attorney, Agent, or Firm*—Crowell & Moring LLP

(57) ABSTRACT

The present invention relates to a polymerizable monomer represented by the general formula (1),

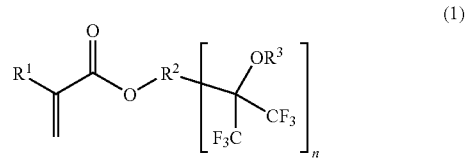

(1)

wherein $R^1$ is a hydrogen atom, a halogen atom, a hydrocarbon group or a fluorine-containing alkyl group; $R^2$ is a straight-chain or branched alkyl group, a cyclic alkyl group, an aromatic group, or a substituent having at least two of these groups, the $R^2$ being optionally partially fluorinated; $R^3$ is a hydrogen atom, a hydrocarbon group that is optionally branched, a fluorine-containing alkyl group, or a cyclic group having an aromatic or alicyclic structure, the $R^3$ optionally containing a bond of an oxygen atom or carbonyl group; and n is an integer of 1-2.

40 Claims, No Drawings

FLUORINE-CONTAINING POLYMERISABLE MONOMER AND POLYMER PREPARED BY USING SAME

CROSS REFERENCE TO RELATED APPLICATIONS

This application is a division of application Ser. No. 10/880,097, filed Jun. 30, 2004, now U.S. Pat. No. 7,094,850, which is a division of application Ser. No. 10/198,044, filed Jul. 19, 2002, now U.S. Pat. No. 6,784,312, the entire disclosures of which are incorporated herein by reference.

BACKGROUND OF THE INVENTION

The present invention relates to (a) novel fluorine-containing monomers having a special structure, that is, a hydroxyl group or a substituent for protecting or modifying hydroxyl group, (b) polymers prepared by polymerization or copolymerization of such monomers, and (c) materials (e.g., reflection preventive materials, photosensitive coatings, and resist materials) containing such polymers.

Fluorine-containing compounds have been used and developed in various fields particularly in the field of advanced materials due to their good qualities (e.g., water repellency, oil repellency, low water absorption, heat resistance, weather resistance, corrosion resistance, transparency, photosensitivity, low refractive index, and low dielectric property). In particular, there have been active researches and developments of fluorine-containing compounds in the fields of (a) reflection preventive films utilizing low refractive index and visible light transparency of fluorine-containing compounds, (b) optical devices utilizing transparency of fluorine-containing compounds in a long wavelength band for optical communication, and (c) resist materials utilizing transparency of fluorine-containing compounds in ultraviolet region (particularly vacuum ultraviolet wavelength region). In these fields, the common task of designing polymers is to achieve adhesion to the substrate and high glass transition point (hardness), while achieving transparency at each wavelength for use by introducing as many fluorine atoms as possible into the polymer. Although there have been various proposals for increasing transparency at each wavelength by increasing the fluorine content in the polymer, there is no or very few proposals for improving water repellency and adhesion and for obtaining higher glass transition point by newly designing fluorine-containing monomers themselves. Recently, there have been some reports of hydroxyl group-containing and fluorine-containing styrenes and hydroxyl group-containing and fluorine-containing norbornene compounds in the field of the next generation $F_2$ resist in vacuum ultraviolet region. However, there are demands for new materials (i.e., novel polymers and novel monomers for providing novel polymers) having a sufficiently low refractive index necessary for reflection preventive films, for those having a sufficient transparency at optical communication wavelength, and for those having both of a sufficient transparency in ultraviolet region and a sufficient etching resistance.

SUMMARY OF THE INVENTION

It is an object of the present invention to provide a novel polymerizable monomer capable of providing polymers that have (a) high transparency in a wide wavelength region from vacuum ultraviolet region to optical communication wavelength region, (b) improved adhesion to the substrate, and (c) improved film forming property.

According to the present invention, there is provided a polymerizable monomer represented by the general formula (1),

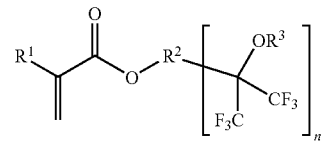

wherein $R^1$ is a hydrogen atom, a halogen atom, a hydrocarbon group or a fluorine-containing alkyl group;

$R^2$ is a straight-chain or branched alkyl group, a cyclic alkyl group, an aromatic group, or a substituent having at least two of these groups, said $R^2$ being optionally partially fluorinated;

$R^3$ is a hydrogen atom, a hydrocarbon group that is optionally branched, a fluorine-containing alkyl group, or a cyclic group having an aromatic or alicyclic structure, said $R^3$ optionally containing a bond of an oxygen atom or carbonyl group; and n is an integer of 1-2.

DESCRIPTION OF THE PREFERRED EMBODIMENTS

The above-mentioned novel polymerizable monomer according to the present invention is a fluorine-containing acrylate derivative having a high fluorine content and a hydroxyl group or a substituent ($R^3$) for protecting or modifying the hydroxyl group. The inventors unexpectedly found that polymers prepared by polymerization or copolymerization using the novel polymerizable monomer have (a) high transparency in a wide wavelength region from vacuum ultraviolet region to optical communication wavelength region, (b) improved adhesion to the substrate, and (c) improved film forming property. Therefore, the resulting polymers are very useful for reflection preventive materials, optical device materials and resist materials. Furthermore, the polymerizable monomer, which is an acrylic monomer, is easy to be handled in an industrial scale production.

The novel polymerizable monomer, represented by the general formula (1), has fluorine and hydroxyl group coexistent in its hexafluoroisopropanol group. As defined above, $R_1$ usable in the general formula (1) can be selected from hydrogen atom, halogen atoms, hydrocarbon groups and fluorine-containing alkyl groups. Of these, preferable halogen atoms are fluorine, chlorine and bromine. Preferable hydrocarbon groups are methyl group, ethyl group, propyl group, isopropyl group, butyl group, isobutyl group, sec-butyl group, tert-butyl group, cyclopentyl group, cyclohexyl group, phenyl group, benzyl group, and phenethyl group. Examples of the fluorine-containing alkyl groups are those containing fluorine atom partially or totally substituted for hydrogen atom of the above-cited alkyl groups. In the case of the hydrocarbon groups and the fluorine-containing alkyl groups, the number of carbon atoms in the molecule is preferably about 1-20, preferably 1-4 from the viewpoint of polymerizability of the monomer. Exemplary fluorine-containing groups are trifluoromethyl group (—$CF_3$), trifluoroethyl group (—$CH_2CF_3$), 1,1,1,3,3,3-hexafluoroisopropyl group, heptafluoroisopropyl group, and nonafluoro-n-butyl group (—$C_4F_9$).

As stated above, $R^2$ usable in the general formula (1) can be a straight-chain or branched alkyl group, a cyclic alkyl group, an aromatic group, or a substituent having at least two of these groups. Furthermore, $R^2$ is optionally partially fluorinated and optically contains an unsaturated bond(s). Examples of $R^2$ are straight-chain or branched alkylene groups such as methylene group, ethylene group, isopropylene group and t-butylene group; cyclic groups such as cyclobutene group, cyclohexane group, norbornene group and adamantane group; and aromatic groups such as phenyl group.

Specific examples of the polymerizable monomer (represented by the general formula (1)) are represented by the following general formulas (2)-(5):

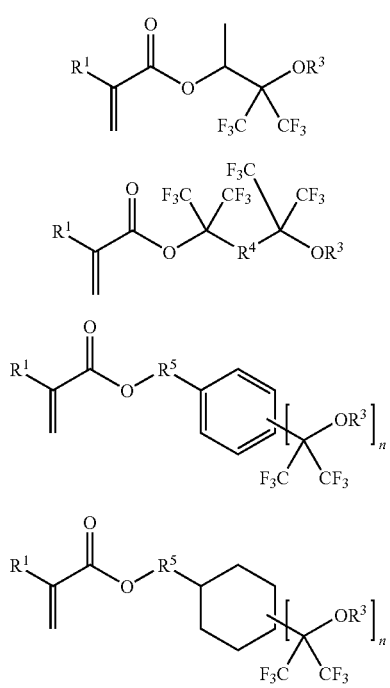

wherein $R^3$ is a hydrogen atom, a hydrocarbon group that is optionally branched, a fluorine-containing alkyl group, or a cyclic group having an aromatic or alicyclic structure, and $R^3$ optionally contains a bond of an oxygen atom or carbonyl group. If $R^3$ is a hydrogen atom, the resulting polymer is improved in transparency. However, depending on the use of the resulting polymer, $R^3$ can be selected from the other groups. Examples of such groups are hydrocarbon groups having a carbon atom number of about 1-20 and optionally having a cyclic structure, such as methyl group, ethyl group, isopropyl group, cyclopropyl group, cyclopentyl group, cyclohexyl group, norbornel group, adamantyl group and benzyl group. Further exemplary oxygen atom-containing groups are open-chain ether groups such as methoxymethyl ether and methoxyethoxymethyl ether; cyclic ether groups such as tetrahydrofuran and tetrahydropyrane; and aromatic groups such as 4-methoxybenzyl group. Further exemplary carbonyl-containing groups are acetyl group, pivaloyl group, tert-butoxycarbonyl group, and benzoyl group. It is possible to protect or modify the carbonyl-containing groups. Its purpose is to provide the polymers, for example, with (a) crosslinking property, (b) positive-type photosensitivity by a photo-induced acid generator, and (c) etching resistance, thereby producing the polymers having a good solubility in organic solvents and alkali aqueous solutions, a high glass transition point, and a heat resistance upon soldering. Thus, $R^3$ can suitably be selected depending on the use of the polymer.

$R^4$ in the general formula (3) can be a hydrocarbon group having a carbon atom number of 1-20. Its examples are open-chain hydrocarbon groups such as methylene, ethylene and isopropylene; and cyclic hydrocarbon groups such as cyclopropyl, cyclopentyl, cyclohexyl and norbornel and adamantyl. The hydrocarbon group may be partially replaced with, for example, fluorine, bromine and chlorine. Further exemplary oxygen-containing groups are $C_3$-$C_5$ cyclic ethers, $C_1$-$C_{20}$ straight-chain or branched alkyl groups. Further exemplary aromatic groups are phenyl group, diphenyl ether group, trifluoromethylphenyl group, and ditrifluoromethylphenyl groups. Furthermore, $R^4$ may have an unsaturated bond(s).

$R^5$ in the general formulas (4) and (5) can be a hydrocarbon group having a carbon atom number of 1-5. Its examples are open-chain hydrocarbon groups such as methylene, ethylene, isopropylene, butylene, isobutylene, and sec-butylene; and cyclic hydrocarbon groups such as cyclopropyl, cyclopentyl, cyclohexyl, norbornel, and adamantyl.

The method for synthesizing the α,β-unsaturated esters, which are represented by the general formulas (1)-(5), is not particularly limited. For example, they can be synthesized by a condensation of an alcohol (derived from hexafluoroacetone) with an α,β-unsaturated carboxyl acid (e.g., acrylic acid, methacrylic acid, 2-trifluoromethyl acrylic acid, 2-nonafluoro-n-buthyl acrylic acid) or α,β-unsaturated carboxylic halide (e.g., acrylic chloride, methacrylic chloride, 2-trifluoromethylacrylic chloride, and 2-nonafluoro-n-butylacrylic chloride). As another example, they can be synthesized by an addition reaction of a double bond-containing compound (derived from hexafluoroacetone) with an α,β-unsaturated carboxylic acid (e.g., acrylic acid, methacrylic acid, 2-trifluoromethylacrylic acid, and 2-nonafluoro-n-butylacrylic acid) in the presence of a Lewis acid (e.g., sulfuric acid, hydrochloric acid, methanesulfonic acid, and trifluoromethanesulfonic acid).

The reaction product after each reaction can be purified by a known method such as concentration, distillation, extraction, recrystallization, filtration, and column chromatography. It is optional to combine at least two of the purification procedures.

The polymer according to the present invention can be (a) a homopolymer prepared by polymerizing one of the abovementioned polymerizable monomers represented by the general formulas (1)-(5), or (b) a copolymer prepared by copolymerizing at least two of the polymerizable monomers represented by the general formulas (1)-(5), or (c) another copolymer prepared by copolymerizing at least one of the polymerizable monomers represented by the general formulas (1)-(5) with another comonomer.

The another comonomer is preferably at least one selected from olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

Exemplary olefins for the another comonomer are ethylene and propylene. Exemplary fluorine-containing olefins for that are vinyl fluoride, vinylidene fluoride, trifluoroethylene, chlorotrifluoroethylene, tetrafluoroethylene, hexafluoropropylene, and hexafluoroisobutene.

Exemplary (meth)acrylic esters (i.e., acrylic esters and methacrylic esters) for that are not particularly limited with respect to their ester side chains. They are (meth)acrylic alkyl esters such as methyl(meth)acrylate, ethyl(meth)acrylate, n-propyl(meth)acrylate, isopropyl(meth)acrylate, n-butyl (meth)acrylate, isobutyl(meth)acrylate, n-hexyl(meth)acrylate, n-octyl(meth)acrylate, 2-ethylhexyl(meth)acrylate, lauryl(meth)acrylate, 2-hydroxyethyl(meth)acrylate, and 2-hydroxypropyl(meth)acrylate; (meth)acrylates containing groups such as ethylene glycol, propylene glycol and tetramethylene glycol; unsaturated amides such as (meth)acrylic amide, N-methylol(meth)acrylic amide, and diacetoneacrylic amide; (meth)acrylonitrile, alkoxysilane-containing vinyl silanes and (meth)acrylic esters, t-butyl(meth)acrylate, and cyclic (meth)acrylate such as 3-oxocyclohexyl(meth)acrylate, adamantyl(meth)acrylate, alkyladamantyl(meth)acrylate, cyclohexyl(meth)acrylate, tricyclodecanyl(meth)acrylate and (meth)acrylate having cyclic structures such as lactone ring and norbornene ring; and (meth)acrylic acid. Further examples are $\alpha$-cyano group-containing (meth)acrylate and analogous compounds such as maleic acid, fumaric acid and maleic anhydride.

The fluorine-containing (meth)acrylic esters may have a fluorine-containing group at their $\alpha$-position or ester moiety. Furthermore, they may have a cyano group at the $\alpha$-position. Such fluorine-containing groups at their $\alpha$-position may be trifluoromethyl group, trifluoroethyl group and nonafluoro-n-butyl group.

Further exemplary fluorine-containing (meth)acrylic esters may have at their ester moiety a fluoroalkyl or perfluoroalkyl group or a fluorine-containing cyclic structure. This cyclic structure may have a substituent (e.g., fluorine and trifluoromethyl group), and its examples are fluorine-containing benzene ring, fluorine-containing cyclopentane ring, fluorine-containing cyclohexane ring, and fluorine-containing cycloheptane ring. Further exemplary (meth)acrylic esters may have at their ester moiety a fluorine-containing t-butyl ester group. Concrete examples of the fluorine-containing (meth)acrylic ester are 2,2,2-trifluoroethyl(meth) acrylate, 2,2,3,3-tetrafluoropropyl(meth)acrylate, 1,1,1,3,3, 3-hexafluoroisopropyl(meth)acrylate, heptafluoroisopropyl (meth)acrylate, 1,1-dihydroheptafluoro-n-butyl(meth) acrylate, 1,1,5-trihydrooctafluoro-n-pentyl(meth)acrylate, 1,1,2,2-tetrahydrotridecafluoro-n-octyl(meth)acrylate, 1,1,2, 2-tetrahydroheptadecafluoro-n-decyl(meth)acrylate, perfluorocyclohexylmethylacrylate, and perfluorocyclohexylmethylmethacrylate.

The above-mentioned norbornene compounds and fluorine-containing norbornene compounds may have a mononucleus or multinucleus structure. It is possible to copolymerize these norbornene compounds with the above-mentioned polymerizable monomers represented by the general formulas (1)-(5), without any particular limitations. It is preferable to prepare the norbornene compounds by a Diels-Alder addition reaction of unsaturated compounds (e.g., allyl alcohol, fluorine-containing allyl alcohol, acrylic acid, $\alpha$-fluoroacrylic acid, methacrylic acid, and all of the above-mentioned (meth)acrylic esters and fluorine-containing (meth)acrylic esters) to dienes (e.g., cyclopentadiene and cyclohexadiene).

Further examples of the above-mentioned another comonomer are styrene compounds and fluorine-containing styrene compounds, such as styrene, fluorinated styrene, hydroxystyrene, hexafluoroacetone-added styrene compounds, and styrene and hydroxystyrene each containing trifluoromethyl group substituted for hydrogen. These styrene compounds and fluorine-containing styrene compounds may have at their $\alpha$-position a halogen, an alkyl group or a fluorine-containing alkyl group.

Still further examples of the above-mentioned another comonomer are vinyl ethers, fluorine-containing vinyl ethers, allyl ethers, vinyl esters, and vinyl silanes. It is possible to copolymerize vinyl ethers, fluorine-containing vinyl ethers, allyl ethers and vinyl esters with the polymerizable monomers (represented by the general formulas (1)-(5)) by suitably adjusting relative amounts of these monomers and comonomers used in the copolymerization. For example, the another comonomer may be an alkyl vinyl ether that optionally contains methyl group, ethyl group or hydroxy group (e.g., hydroxyethyl group and hydroxybutyl group) and that optionally contains fluorine substituted for a part or all of the hydrogen atoms. The another comonomer may be cyclohexyl vinyl ether or another cyclic vinyl ether containing hydrogen or carbonyl bond in its cyclic structure. Such cyclic vinyl ether may contain fluorine substituted for a part or all of the hydrogen atoms. Furthermore, allyl ethers, vinyl esters and vinyl silanes for the another comonomer can be selected from known compounds without any particular limitation upon use.

It is optional to use a single comonomer or a combination of at least two comonomers. Upon the polymerization, the ratio of the polymerizable monomer to the another comonomer is not particularly limited. The amount of the former is preferably from 10-100%, more preferably 30-100%. If it is less than 30%, the resulting polymer may become insufficient in transparency or film-forming property depending on the wavelength range for use.

The polymerization or copolymerization method for obtaining the target polymer is not particularly limited. For example, it is preferable to use radical polymerization or ionic polymerization. In some cases, it is also possible to use coordinated anionic polymerization or living anionic polymerization.

Particulars of the above-mentioned radical polymerization are as follows. The radical polymerization can be conducted by a known manner such as bulk polymerization, solution polymerization, suspension polymerization or emulsion polymerization by a batch-wise, half-continuous or continuous operation.

The radical polymerization initiator is not particularly limited. Its examples are azo compounds, peroxides and redox compounds. Of these, azobisbutyronitrile, t-butylperoxypivalate and benzoyl peroxide are preferable.

The reaction vessel for conducting the polymerization (copolymerization) is not particularly limited. It is optional to use a solvent for conducting the polymerization. The polymerization solvent is preferably one that does not interfere with the radical polymerization. Its typical examples are esters such as ethyl acetate and n-butyl acetate; ketones such as acetone and methyl isobutyl ketone; hydrocarbons such as toluene and cyclohexane; and alcohols such as isopropyl alcohol and ethylene glycol monomethyl ether. Furthermore, it can be selected from various other solvents such as water, ethers, cyclic ethers, fluorohydrocarbons, and aromatic solvents. It is optional to use a single solvent or a mixture of at least two solvents. Furthermore, it is possible to use a molecular weight adjusting agent, such as mercaptan, in the polymerization. The temperature for conducting the polymerization may be suitably adjusted depending on the type of radical polymerization initiator or radical polymerization initiating source. It is preferably 20-200° C., particularly preferably 30-140° C.

After the polymerization, it is possible to remove the reaction medium (i.e., organic solvent or water) from the solution or dispersion of the target polymer by a known method. For example, it can be conducted by reprecipitation followed by filtration, or by heating under vacuum to distill the medium off.

The target polymer according to the present invention may have a number average molecular weight of 1,000-100,000, preferably 3,000-50,000.

The polymer according to the present invention may be formed into a film by dissolving the polymer in a solvent to prepare a coating solution and then by applying the coating solution to a substrate. This solvent is not particularly limited as long as the polymer can be dissolved therein. Its examples are ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, and ethers (monomethyl ether, monoethyl ether, monopropyl ether, monobutyl ether and monophenyl ether) of dipropylene glycol monoacetate, and derivatives of polyhydric alcohols; cyclic ethers such as dioxane; esters such as methyl lactate, ethyl lactate, methyl acetate, ethyl acetate, butyl acetate, methylpyruvate, ethyl pyruvate, methyl methoxypropionate, and ethyl ethoxypropionate; aromatic solvents such as xylene and toluene; and fluorine-containing solvents such as fleon, alternative fleon, perfluoro compounds, and hexafluoroisopropyl alcohol. Furthermore, it is possible to use a high-boiling-point, weak solvent (e.g., a perpene-based petroleum naphtha solvent or paraffinic solvent) for the purpose of increasing coatability (applicability of the coating solution). The solvent for preparing the coating solution may be a single solvent or a mixture of at least two solvents.

It is possible to form a reflection preventive film on the surface of a substrate (e.g., glass, plastic, liquid crystal panel, plasma display panel, and electroluminescence panel) by applying the polymer of the present invention thereto to have an ultra-thin thickness. The reflection preventive film can be a single layer of this polymer or a laminate of at least one layer of this polymer and at least one layer of another material having a refractive index different from that of this polymer. In order to enhance its reflection preventive capability, it is preferable to adjust refractive index of the polymer in a visible light region to 1.42 or lower, more preferably 1.4 or lower. As the fluorine content of the polymer increases, the refractive index becomes lower. With higher fluorine content, its adhesion to substrate tends to lower. In this case, it is possible to increase adhesion by using a reflection preventive film prepared by polymerizing a monomer that is represented by one of the general formulas (1)-(5) and that has an alcohol side chain in which $R^3$ is a hydrogen. The thickness of the reflection preventive film may be varied depending on the refractive index of the substrate. It may be in a range of 50-200 nm.

It is possible to produce optical devices by using the polymer according to the present invention. For example, it is possible to produce an optical waveguide for wavelengths of 650-1,550 nm, preferably one for wavelengths of 850-1,550 nm that is relatively transparent to a light source used in semiconductor laser or in optical fiber for communication. It is possible to produce an optical waveguide (e.g., of a slab-type) by using the polymer for at least one of its core and cladding. For example, it is possible to produce an optical waveguide by a method comprising the sequential steps of (a) forming a lower cladding of a polymer according to the present invention; (b) coating the lower cladding with another polymer according to the present invention having a refractive index higher than that of the lower cladding; (c) partially irradiating the another polymer with light directly or using a mask to form a latent image; (d) removing the unirradiated portion of the another polymer by a solvent to form a core of a certain pattern; and (e) forming on the lower cladding an upper cladding of a polymer according to the present invention having a refractive index lower than that of the core in a manner that the core is embedded in the upper cladding, followed by heating or ultraviolet irradiation.

It is also possible to produce an optical waveguide by another similar method comprising the sequential steps of (a) forming a lower cladding layer; (b) forming thereon a core layer (flat film); (c) patterning the core layer using a photoresist; (d) forming a core ridge through reactive ion etching; and (e) forming thereon an upper cladding.

Generally speaking, optical devices are required to have heat resistance upon soldering since they are usually mounted on electrical devices or wiring substrates. According to the present invention, it is possible to provide the polymer with such heat resistance by (a) using a polymerizable monomer that is represented by one of the general formulas (1)-(5) and that has an alcohol side chain (hydroxyl group) in which $R^3$ is a hydrogen and by (b) subjecting the hydroxyl group to a crosslinking reaction. A usable hardener for hardening the polymer is not particularly limited. Its examples are polyisocyanate and epoxy compounds, compounds containing a plurality of carboxyl groups in the molecule. It is possible to produce a negative-type light sensitive polymer by polymerizing the above polymerizable monomer in which $R^3$ is an ester moiety prepared by an esterification between a side chain hydroxyl group and a (meth)acrylic acid or (meth)acrylic chloride. The resulting polymer can be used for various fields such as optical devices, reflection preventive film and resist.

It is possible to produce a novel resist composition by using the polymer according to the present invention. It is the most preferable to use this polymer for producing a positive-type resist composition. In fact, this resist composition contains (a) a polymer according to the present invention, of which solubility in alkali aqueous solution changes by the action of acid, and (b) an acid generator. This resist composition is preferably used, for example, for preparing semiconductors using a 193 nm ArF eximer laser or vacuum ultraviolet (typically 157 nm) $F_2$ laser. In fact, the polymer, of which solubility in alkali aqueous solution changes by the action of acid, is characterized in that $R^2$, $R^3$ and $R^5$ in the general formulas (1)-(5) are acid-labilized groups (i.e., groups to be labilized by acid). This polymer is not further particularly limited in its structure. This polymer can be prepared from a monomer (represented by one of the general formulas (1)-(5)) in which $R^2$ has a tert-butyl structure as an acid-labilized group and in which its ester moiety is severed by an acid. Exemplary acid-labilized groups for $R^3$ are tert-butyl group, tert-butoxycarbonyl group, open-chain and cyclic ether groups, and lactone group having a cyclic structure. The above polymer is insoluble or very slightly soluble in alkali aqueous solution prior to the activating energy ray irradiation. The activating energy ray irradiation, however, generates an acid from the acid generator. Then, the polymer is hydrolyzed by this acid and thereby becomes soluble in alkali aqueous solution.

The above-mentioned acid generator for a resist composition is not particularly limited. It can be suitably selected from acid generators for chemically amplified resists. Preferable examples of such acid generators are fluorine-containing sulfonic acid derivatives and fluorine-containing sulfonylimide derivatives. Preferable salts for the actual use as acid generators are bissulfonyldiazomethanes, nitrobenzyl derivatives, onium salts, halogen-containing triazine compounds, cyano group-containing oximesulfonate compounds, and other oximsulfonate compounds. The acid generator may be used in the form of a single compound or a mixture of at least two compounds. The content of the acid generator in the resist composition may be 0.5-20 parts by weight, relative to 100 parts by weight of the polymer. If it is less than 0.5 parts by weight, the resist composition may become insufficient in image forming capability. If it is greater than 20 parts by weight, it may become difficult to prepare a uniform solution of the resist composition. Thus, the resulting solution may become inferior in storage stability.

The above-mentioned resist composition according to the present invention can be used in conventional resist patterning methods, as exemplified in the following. Firstly, a solution of the resist composition is applied to a supporting member (e.g., silicon wafer) by spin coating or the like, followed by drying to form a photosensitive layer. Then, the photosensitive layer is exposed to an eximer laser light from an exposure apparatus through a desired mask pattern, followed by heating. Then, a development treatment is conducted by using, for example, an alkali aqueous solution such as 0.1-10 wt % tetramethylammonium hydroxide aqueous solution, thereby obtaining a resist pattern conforming to the mask pattern.

According to need, it is optional to add a miscible additive to the polymer. Examples of such additive are additional resins, quencher, plasticizer, stabilizer, coloring agent, surfactant, tackifier, leveling agent, deforming agent, compatibility enhancing agent, adhesion enhancing agent, and antioxidant.

The following nonlimitative Examples are illustrative of the present invention. Polymerizable monomers according to the present invention were synthesized by the following Synthesis Examples 1-6.

Synthesis Example 1

Synthesis of α-$C_4F_9$ Acrylate Represented by the Following Formula (6)

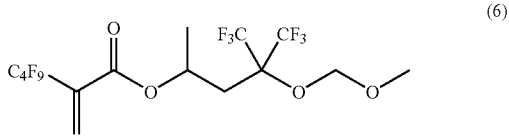

(6)

Under nitrogen atmosphere, 18.5 ml of toluene were added at room temperature to 1.00 g (3.70 mmol) of 1,1,1-trifluoro-2-(trifluoromethyl)-2-(methoxymethyl ether)pentane-4-ol in a 50 ml three-necked flask to dissolve the same. Then, 97.7 mg (4.07 mmol) of sodium hydride was added to the solution at 0° C., followed by stirring at 50° C. for 2 hr. Then, a solution prepared by dissolving 1.26 g (4.07 mmol) of 2-nonafluoro-n-butylacrylic chloride in 1.5 ml of toluene was added in a dropwise manner at 0° C., followed by stirring at room temperature for 7 hr. To the resulting reaction solution, a suitable amount of a saturated ammonium chloride aqueous solution was added at 0° C. to decompose the reagent, followed by dilution with an excessive amount of ether. The resulting organic layer was washed with saturated ammonium chloride aqueous solution, saturated sodium hydrogencarbonate aqueous solution, ion exchanged water, and saturated brine. The thus washed organic layer was dried with a suitable amount of magnesium sulfate, and then concentrated under vacuum with an evaporator.

Then, the obtained product (mixture) was purified by a silica gel column chromatography (ethyl acetate/n-hexane=0/1-1/10), thereby obtaining 1.46 g (2.69 mmol) of a purified product. This purified product was confirmed by nuclear magnetic resonance analysis as being an α-$C_4F_9$ acrylate having the above formula (6).

Synthesis Example 2

Synthesis of a Methacrylate Represented by the Following Formula (7)

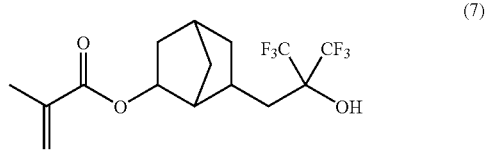

(7)

Under nitrogen atmosphere, there were mixed at room temperature in a 50 ml three-necked flask 5.00 g (17.11 mmol) of 3-(5-hydroxybicyclo[2.2.1]heptane)-1,1,1-trifluoro-2-(trifluoromethyl)-2-propanol, 1.91 g (22.24 mmol) of methacrylic acid, and 18.8 mg (0.17 mmol) of hydroquinone. Then, 2.52 g (25.67 mmol) of concentrated sulfuric acid were added in a dropwise manner at 0° C., followed by stirring at 70° C. for 6 hr. Then, a large amount of ion exchanged water was added at 0° C. for dilution. The resulting reaction mixture was extracted with a suitable amount of diethyl ether. Then, the obtained organic layer was washed with ion exchanged water and saturated brine. The thus washed organic layer was dried with magnesium sulfate, and then concentrated under vacuum with an evaporator.

Then, the obtained product (mixture) was purified by a silica gel column chromatography (ethyl acetate/n-hexane=1/10-1/3), thereby obtaining 4.13 g (11.46 mmol) of a purified product. This purified product was confirmed by nuclear magnetic resonance analysis as being a methacrylate having the above formula (7).

Synthesis Example 3

Synthesis of an α-Trifluoromethylacrylate Represented by the Following Formula (8)

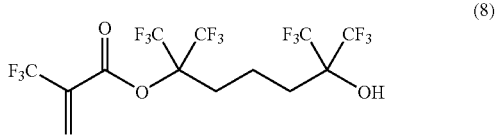

(8)

Under nitrogen atmosphere, there were mixed at room temperature in a 50 ml three-necked flask 3.00 g (7.97 mmol) of 1,1,1,7,7,7-hexafluoro-2-(trifluoromethyl)-6-(trifluoromethyl)heptane-1,6-diol, 1.45 g (10.37 mmol) of α-trifluoromethylacrylic acid, and 8.7 mg (0.08 mmol) of hydroquinone. Then, 1.17 g (11.96 mmol) of concentrated sulfuric acid were added in a dropwise manner at 0° C., followed by stirring at 70° C. for 15 hr. Then, a large amount of ion exchanged water was added at 0° C. for dilution. The resulting reaction mixture was extracted with a suitable amount of diethyl ether. Then, the obtained organic layer was washed with ion exchanged water and saturated brine. The thus washed organic layer was dried with magnesium sulfate, and then concentrated under vacuum with an evaporator.

Then, the obtained product (mixture) was purified by a silica gel column chromatography (ethyl acetate/n-hexane=1/

15-1/5-1/2), thereby obtaining 1.63 g (3.26 mmol) of a purified product. This purified product was confirmed by nuclear magnetic resonance analysis as being an α-trifluoromethylacrylate having the above formula (8).

Synthesis Example 4

Synthesis of α-Trifluoromethylacrylate Represented by the Following Formula (9)

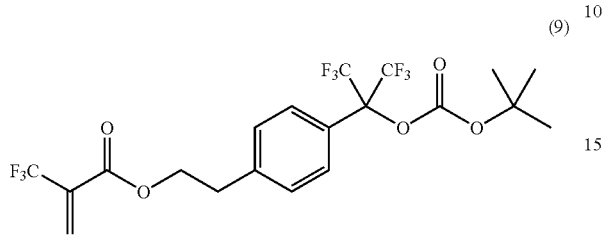

(9)

Under nitrogen atmosphere, 1.00 g (2.57 mmol) of 4-(hexafluoroisopropyl-tert-butoxycarbonylester)phenethyl alcohol was dissolved at room temperature in 25.7 ml of methylene chloride in a 50 ml three-necked flask. Then, 1.10 ml (7.73 mmol) of triethylamine were added to the solution at 0° C. Then, 0.61 g (3.86 mmol) of α-trifluoromethylacrylic chloride were added in a dropwise manner. Then, 31.5 mg (0.26 mmol) of 4-dimethylaminopyridine were added at 0° C., followed by stirring at 0° C. for 20 minutes. Then, a suitable amount of ion exchanged water was added to the reaction liquid, followed by extraction with a suitable amount of diethyl ether. The resulting organic layer was washed with ion exchanged water and saturated brine. The thus washed organic layer was dried with a suitable amount of magnesium sulfate, and then concentrated under vacuum with an evaporator.

Then, the obtained product (mixture) was purified by an activated alumina (neutral) column chromatography (ethyl acetate/n-hexane=1/10), thereby obtaining 1.19 g (2.34 mmol) of a purified product. This purified product was confirmed by nuclear magnetic resonance analysis as being an α-trifluoromethylacrylate having the above formula (9).

Synthesis Example 5

Synthesis of an Acrylate Represented by the Following Formula (10)

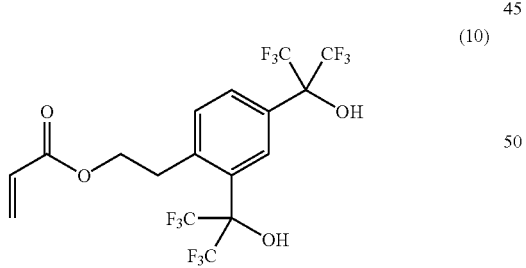

(10)

Under nitrogen atmosphere, there were mixed at room temperature in a 50 ml three-necked flask 1.00 g (2.20 mmol) of 2,4-dihexafluoroisopropanolphenethyl alcohol, 0.24 g (3.30 mmol) of acrylic acid, and 2.4 mg (0.02 mmol) of hydroquinone. Then, 0.39 g (3.96 mmol) of concentrated sulfuric acid were added in a dropwise manner at 0° C., followed by stirring at 70° C. for 6 hr. Then, a large amount of ion exchanged water was added at 0° C. for dilution. The resulting reaction mixture was extracted with a suitable amount of diethyl ether. Then, the obtained organic layer was washed with ion exchanged water and saturated brine. The thus washed organic layer was dried with magnesium sulfate, and then concentrated under vacuum with an evaporator.

Then, the obtained product (mixture) was purified by a silica gel column chromatography (ethyl acetate/n-hexane=1/10-1/1-3/1), thereby obtaining 0.91 g (1.80 mmol) of a purified product. This purified product was confirmed by nuclear magnetic resonance analysis as being an acrylate having the above formula (10).

Synthesis Example 6

Synthesis of an α-Trifluoromethylacrylate Represented by the Following Formula (11)

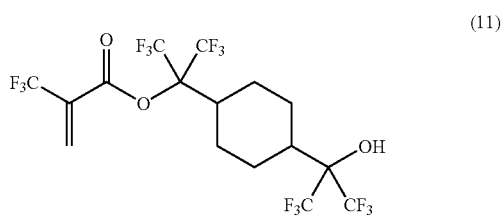

(11)

Under nitrogen atmosphere, there were mixed at room temperature in a 50 ml three-necked flask 5.00 g (16.99 mmol) of 4-(hexafluoroisopropanol)cyclohexaneethanol, 1.85 g (22.09 mmol) α-trifluoromethylacrylic acid, and 18.7 mg (0.17 mmol) of hydroquinone. Then, 6.80 g (25.48 mmol) of fuming sulfuric acid (30% $SO_3$) were added in a dropwise manner at 0° C., followed by stirring at 70° C. for 5 hr. Then, a large amount of iced water was added little by little at 0° C. for dilution. The resulting reaction mixture was extracted with a suitable amount of diethyl ether. Then, the obtained organic layer was washed with ion exchanged water and saturated brine. The thus washed organic layer was dried with magnesium sulfate, and then concentrated under vacuum with an evaporator.

Then, the obtained product (mixture) was purified by a silica gel column chromatography (ethyl acetate/n-hexane=1/10-1/2), thereby obtaining 6.15 g (14.78 mmol) of a purified product. This purified product was confirmed by nuclear magnetic resonance analysis as being an α-trifluoromethylacrylate having the above formula (11).

Synthesis Example 7

Synthesis of a Homopolymer of α-$C_4F_9$ Acrylate Represented by the Following Formula (12)

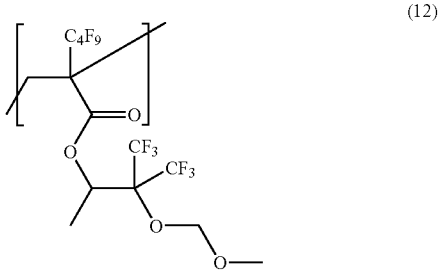

(12)

Under argon atmosphere, 1.00 g of α-$C_4F_9$ acrylate of the formula (6) was dissolved at room temperature in 7.00 ml of tetrahydrofuran in a 20 ml round-bottom flask. Then, 0.5 mol % 1,1-diphenylhexyllithium tetrahydrofuran solution was added in a dropwise manner at −78° C., followed by stirring at −78° C. for 12 hr. The resulting polymer was reprecipitated from the polymerization liquid at room temperature using an excessive amount of n-hexane and then recovered by filtration. The obtained polymer was dried under vacuum for 12 hr in an oven of 80° C., thereby obtaining 0.91 g of a homopolymer of an α-C$_4$F$_9$ acrylate represented by the above formula (12). Its molecular weight was determined by using polystyrene as a standard material. With this, its number average molecular weight (Mn) and its weight average molecular weight (Mw) were respectively 6000 and 11000.

Synthesis Example 8

Synthesis of a Homopolymer of a Methacrylate Represented by the Following Formula (13)

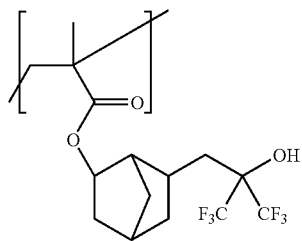

(13)

Under nitrogen atmosphere, 1.00 g of a methacrylate of the formula (7) was dissolved at room temperature in 1.00 g of tetrahydrofuran in a 20 ml round-bottom flask. Then, 2.2 mg (0.5 mol %) of α,α'-azobisisobutyronitrile were added at room temperature, followed by stirring at 66° C. for 24 hr. The resulting polymer was reprecipitated from the polymerization liquid at room temperature using an excessive amount of n-hexane and then recovered by filtration. The obtained polymer was dried under vacuum for 12 hr in an oven of 80° C., thereby obtaining 0.88 g of a homopolymer of a methacrylate represented by the above formula (13). Its molecular weight was determined by using polystyrene as a standard material. With this, its Mn and Mw were respectively 30000 and 80000.

Synthesis Example 9

Synthesis of a Homopolymer of an α-Trifluoromethylacrylate Represented by the Following Formula (14)

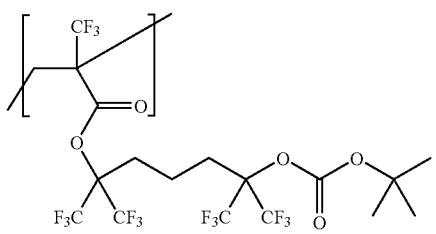

(14)

For preparing a homopolymer of an α-trifluoromethylacrylate represented by the formula (8), its end acid alcohol group was protected as follows.

Under nitrogen atmosphere, 1.60 g (3.21 mmol) of an α-trifluoromethylacrylate of the formula (8) were dissolved at room temperature in 16.0 ml of methylene chloride in a 20 ml round-bottom flask. Then, 0.75 ml (6.42 mmol) of 2,6-lutidine were added at 0° C., followed by addition of 0.84 g (3.85 mmol) of di-tert-butoxydicarbonate at 0° C. and then stirring for 3 hr at 0° C. To the resulting reaction liquid a suitable amount of ion exchanged water was added. The resulting reaction mixture was extracted with a suitable amount of diethyl ether. Then, the obtained organic layer was washed with ion exchanged water and saturated brine. The thus washed organic layer was dried with a suitable amount of magnesium sulfate, and then concentrated under vacuum with an evaporator.

Then, the obtained product (mixture) was purified by a silica gel column chromatography (ethyl acetate/n-hexane=1/10), thereby obtaining 1.79 g (2.99 mmol) of a purified product. This purified product was confirmed by nuclear magnetic resonance analysis as being a tert-butoxycarbonyl ester form of an α-trifluoromethylacrylate of the formula (8).

Then, the purified product was polymerized, as follows. Under argon atmosphere, 1.00 g of the tert-butoxycarbonyl ester form was dissolved at room temperature in 7.00 ml of tetrahydrofuran in a 20 ml round-bottom flask. Then, 0.5 mol % 1,1-diphenylhexyllithium tetrahydrofuran solution was added in a dropwise manner at −78° C., followed by stirring at −78° C. for 12 hr. The resulting polymer was reprecipitated from the polymerization liquid at room temperature using an excessive amount of n-hexane and then recovered by filtration. The obtained polymer was dried under vacuum for 12 hr in an oven of 80° C., thereby obtaining 0.83 g of a homopolymer of an α-trifluoromethylacrylate represented by the above formula (14). Its molecular weight was determined by using polystyrene as a standard material. With this, its number average molecular weight (Mn) and its weight average molecular weight (Mw) were respectively 12000 and 21000.

Synthesis Example 10

Synthesis of a Homopolymer of an α-Trifluoromethylacrylate Represented by the Following Formula (15)

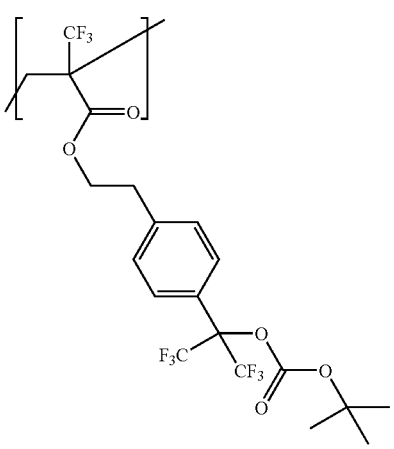

(15)

Under argon atmosphere, 1.00 g of an α-trifluoromethylacrylate was dissolved at room temperature in 7.00 ml of tetrahydrofuran in a 20 ml round-bottom flask. Then, 0.5 mol % 1,1-diphenylhexyllithium tetrahydrofuran solution was added in a dropwise manner at −78° C., followed by stirring at −78° C. for 12 hr. The resulting polymer was reprecipitated from the polymerization liquid at room temperature using an excessive amount of n-hexane and then recovered by filtration. The obtained polymer was dried under vacuum for 12 hr in an oven of 80° C., thereby obtaining 0.90 g of a homopolymer of an α-trifluoromethylacrylate represented by the above formula (15). Its molecular weight was determined by using polystyrene as a standard material. With this, its number average molecular weight (Mn) and its weight average molecular weight (Mw) were respectively 14000 and 19000.

Synthesis Example 11

Synthesis of a Homopolymer of an Acrylate Represented by the Following Formula (16)

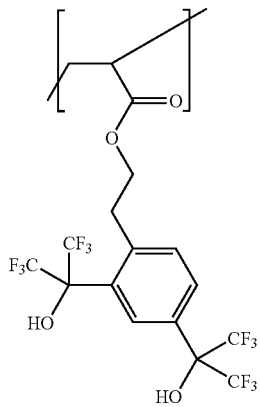
(16)

Under nitrogen atmosphere, 1.00 g of an acrylate of the formula (10) was dissolved at room temperature in 1.00 g of tetrahydrofuran in a 20 ml round-bottom flask. Then, 0.2 mg (0.5 mol %) of α,α'-azobisisobutyronitrile were added at room temperature, followed by stirring at 66° C. for 24 hr. The resulting polymer was reprecipitated from the polymerization liquid at room temperature using an excessive amount of n-hexane and then recovered by filtration. The obtained polymer was dried under vacuum for 12 hr in an oven of 80° C., thereby obtaining 0.78 g of a homopolymer of an acrylate represented by the following formula (16). Its molecular weight was determined by using polystyrene as a standard material. With this, its Mn and Mw were respectively 90000 and 150000.

Synthesis Example 12

Synthesis of a Homopolymer of an α-Trifluoromethylacrylate Represented by the Following Formula (17)

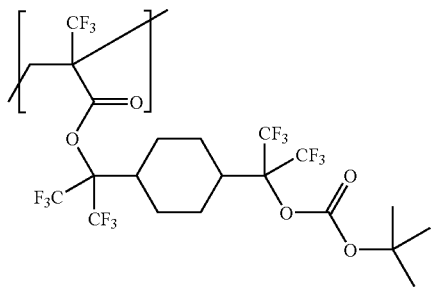
(17)

For preparing a homopolymer of an α-trifluoromethylacrylate represented by the formula (11), its end acid alcohol group was protected as follows.

Under nitrogen atmosphere, 2.00 g (4.80 mmol) of an α-trifluoromethylacrylate of the formula (11) were dissolved at room temperature in 24.0 ml of methylene chloride in a 20 ml round-bottom flask. Then, 1.23 ml (10.57 mmol) of 2,6-lutidine were added at 0° C., followed by addition of 1.57 g (7.2 mmol) of di-tert-butoxydicarbonate at 0° C. and then stirring for 4 hr at 0° C. To the resulting reaction liquid a suitable amount of ion exchanged water was added. The resulting reaction mixture was extracted with a suitable amount of diethyl ether. Then, the obtained organic layer was washed with ion exchanged water and saturated brine. The thus washed organic layer was dried with a suitable amount of magnesium sulfate, and then concentrated under vacuum with an evaporator.

Then, the obtained product (mixture) was purified by a silica gel column chromatography (ethyl acetate/n-hexane=1/10), thereby obtaining 2.01 g (3.88 mmol) of a purified product. This purified product was confirmed by nuclear magnetic resonance analysis as being a tert-butoxycarbonyl ester form of an α-trifluoromethylacrylate of the formula (17).

Then, the purified product was polymerized, as follows. Under argon atmosphere, 1.00 g of the tert-butoxycarbonyl ester form was dissolved at room temperature in 7.00 ml of tetrahydrofuran in a 20 ml round-bottom flask. Then, 0.5 mol % 1,1-diphenylhexyllithium tetrahydrofuran solution was added in a dropwise manner at −78° C., followed by stirring at −78° C. for 12 hr. The resulting polymer was reprecipitated from the polymerization liquid at room temperature using an excessive amount of n-hexane and then recovered by filtration. The obtained polymer was dried under vacuum for 12 hr in an oven of 80° C., thereby obtaining 0.92 g of a homopolymer of an α-trifluoromethylacrylate represented by the following formula (17). Its molecular weight was determined by using polystyrene as a standard material. With this, its number average molecular weight (Mn) and its weight average molecular weight (Mw) were respectively 140000 and 180000.

The results of the syntheses of Synthesis Examples 7-12 are summarized in Table 1.

TABLE 1

| | Synthesis Ex. 7 | Synthesis Ex. 8 | Synthesis Ex. 9 | Synthesis Ex. 10 | Synthesis Ex. 11 | Synthesis Ex. 12 |
|---|---|---|---|---|---|---|
| Raw Material (mol %) | | | | | | |
| Monomer of Synthesis Ex. 1 | 100 | | | | | |

TABLE 1-continued

| | Synthesis Ex. 7 | Synthesis Ex. 8 | Synthesis Ex. 9 | Synthesis Ex. 10 | Synthesis Ex. 11 | Synthesis Ex. 12 |
|---|---|---|---|---|---|---|
| Monomer of Synthesis Ex. 2 | | 100 | | | | |
| Monomer of Synthesis Ex. 3 | | | 100 | | | |
| Monomer of Synthesis Ex. 4 | | | | 100 | | |
| Monomer of Synthesis Ex. 5 | | | | | 100 | |
| Monomer of Synthesis Ex. 6 | | | | | | 100 |
| Yield (%) | 91 | 88 | 83 | 90 | 78 | 92 |
| Mn | 6,000 | 30,000 | 12,000 | 14,000 | 90,000 | 140,000 |
| Mw | 11,000 | 80,000 | 22,000 | 19,000 | 150,000 | 180,000 |
| Solubility | Good | Good | Good | Good | Good | Good |

Synthesis Example 13

Under nitrogen atmosphere, a 150 ml stainless steel autoclave was charged with 1.00 g (40 mol %) of the polymerizable monomer obtained in Synthesis Example 1, 0.62 g (50 mol %) of 4-(hexafluoroisopropanol)styrene, 0.0055 g (10 mol %) of hydroxystyrene, and 16.3 g of butyl acetate. Then, 0.2 mg (0.2 mol %) of α,α'-azobisisobutyronitrile were added at room temperature, followed by stirring at 66° C. for 24 hr. The resulting polymer was reprecipitated from the polymerization liquid at room temperature using an excessive amount of n-hexane and then recovered by filtration. The obtained polymer was dried under vacuum for 12 hr in an oven of 80° C., thereby obtaining 1.11 g of a copolymer represented by the following formula (18). Its molecular weight was determined by using polystyrene as a standard material. With this, its Mn and Mw were respectively 8,000 and 14,000 (see Table 2).

Synthesis Examples 14-19

In each of Synthesis Examples 14-19, Synthesis Example 13 was repeated except in that the composition of the monomers used for preparing the target copolymer was changed as shown in Table 2.

TABLE 2

| | Synthesis Ex. 13 | Synthesis Ex. 14 | Synthesis Ex. 15 | Synthesis Ex. 16 | Synthesis Ex. 17 | Synthesis Ex. 18 | Synthesis Ex. 19 |
|---|---|---|---|---|---|---|---|
| Raw Materials (mol %) | | | | | | | |
| Monomer of Synthesis Ex. 1 | 40 | | | | | | |
| Monomer of Synthesis Ex. 2 | | 55 | | | | | |
| Monomer of Synthesis Ex. 3 | | | 90 | | | | |
| Monomer of Synthesis Ex. 4 | | | | 70 | | | |
| Monomer of Synthesis Ex. 5 | | | | | 60 | | 50 |
| Monomer of Synthesis Ex. 6 | | | | | | 50 | |
| Ethylene | | 5 | | | | | |
| HFIB* | | | | | | | 50 |
| $^t$BuA* | | | | | 5 | | |
| HEMA* | | | | | 5 | | |
| MADMA* | | | | | | 30 | |
| 3FMA* | | | 10 | | | | |
| HSt* | 10 | | | | | | |
| HFIPSt* | 50 | | | | | | |
| VAc* | | 20 | | | | | |
| HFIP-NB* | | | | 30 | | | |
| MA* | | | | | | | 40 |
| CHVE* | | | | | | | 10 |
| $C_8F_{17}$VE* | | 20 | | | | | |
| Yield (%) | 68 | 35 | 87 | 53 | 88 | 65 | 59 |
| Mn | 8,000 | 35,000 | 29,000 | 6,000 | 13,000 | 40,000 | 19,000 |
| Mw | 14,000 | 90,000 | 120,000 | 9,000 | 20,000 | 74,000 | 23,000 |
| Solubility | Good | Good | Good | Good | Good | Good | Good |

*HFIB: Hexafluoroisobutene, $^t$BuA: t-Butyl acrylate, HEMA: Hydroxyethylmethacrylate, MADMA: Methyladamantylmethacrylate, 3FMA: 2,2,2-Trifluoroethylmethacrylate, HSt: 4-Hydroxystyrene, HFIPSt: 1,1,1,3,3,3-Hexafluoro-2-(4-vinylphenyl)-2-propanol, VAc: Vinyl acetate, HFIP-NB: 3-(5-Bicyclo[2.2.1]2-heptenyl)-1,1,1-trifluoro-2-(trifluoromethyl)-2-propanol, MA: Methacrylic acid, CHVE: Cyclohexyl vinyl ether, and $C_8F_{17}$VE: 1H,1H,2H-Perfluoro-n-octyl vinyl ether.

Examples 1-3

In Examples 1-3 respectively, 100 parts by weight of the polymers obtained in Synthesis Examples 8, 14 and 15 were dissolved in methyl isobutyl ketone so that the resulting solutions each had a solid matter concentration of about 30%. Then, a fully methoxylated melamine resin, that is, CYMEL 303 (trade name) of Mitsui Cyanamide Co., was added in an amount of 10 parts by weight per 100 parts by weight of each polymer, followed by a sufficient mixing to prepare three coating liquids.

Then, the coating liquids were each applied to glass plates to form thereon films of 50 µm thickness. Each film was subjected to a natural drying for 1 hr and then to a compulsory drying at 100° C. for 30 min with a hot air dryer to accelerate the crosslinking reaction. The resulting dried films were measured for refractive index using Abbe's refractometer. The results were respectively 1.38, 1.36 and 1.36 in Examples 1-3. The dried films were subjected to a rubbing test by rubbing a cloth moistened with xylene against the dried film by 30 reciprocations. After this test, each dried film was found to have no substantial change on its surface.

Separately, the above solutions (each having a solid matter concentration of about 30%) were each diluted to have a solid matter concentration of about 2%. The resulting solutions were each applied to glass substrates by spin coating so that the resulting films had a thickness of 95-120 nm. With this, it was possible to conduct a uniform spin coating without having cissing or crawling. The resulting films were subjected to a natural drying for 10 min and then to a heat treatment at 100° C. for 1 hr. The resulting coated glass was measured for reflectance at a wavelength of 650 nm. With this, the results were respectively 1.5%, 0.9% and 3.1% in Examples 1-3, showing sufficient reflection preventive properties.

Example 4

Firstly, 100 parts by weight of the polymer obtained in Synthesis Examples 12 were dissolved in methyl isobutyl ketone so that the resulting solution had a solid matter concentration of about 30%. Then, CYMEL 303 was added in an amount of 15 parts by weight per 100 parts by weight of the polymer, followed by a sufficient mixing to prepare a coating liquid.

Then, the coating liquid was applied to a polyethyleneterephthalate (PET) film having a thickness of 100 µm. The resulting film on the PET film was subjected to a natural drying for 1 hr and then to a compulsory drying at 100° C. for 30 min with a hot air dryer. The resulting dried film was measured for refractive index using Abbe's refractometer. The result was 1.37. The dried film was subjected to the same rubbing test as that of Examples 1-3. After this test, the dried film was found to have no substantial change on its surface.

Separately, the above solution (having a solid matter concentration of about 30%) was diluted to have a solid matter concentration of about 2%. The resulting solution was applied to a PET film by spin coating so that the resulting film had a thickness of 95-120 nm. With this, it was possible to conduct a uniform spin coating without having cissing or crawling. The resulting film was subjected to a natural drying for 10 min and then to a heat treatment at 130° C. for 30 min. The resulting coated PET film was measured for reflectance at a wavelength of 650 nm. With this, the result was 1.1%, showing sufficient reflection prevention.

Example 5

In this example, Example 4 was repeated except in that the solution (having a solid matter concentration of about 30%), in place of the coating liquid, was applied to the PET film. The resulting dried film was found to have a refractive index of 1.36. After the rubbing test, the dried film turned to have a white surface. It was judged, however, that the dried film can be used for the application not requiring solvent resistance. Separately, the same spin coating as that of Example 4 was conducted. With this, it was also possible to conduct a uniform spin coating without having cissing or crawling. The resulting film was subjected to a natural drying for 10 min and then to a heat treatment at 130° C. for 30 min. The resulting coated PET film was found to have a reflectance of 0.8%, showing sufficient reflection prevention.

Example 6

Firstly, 100 g of the polymer obtained in Synthesis Example 19 and 12 g of CYMEL 303 were dissolved in 250 g of methyl isobutyl ketone. The resulting solution was applied to a silicon wafer (widths: 6 inches) by spin coating to form a film having a thickness of 25 µm. This film was cured by natural drying and then by a heat treatment at 150° C. for 30 min, thereby forming a lower cladding layer. This cured lower cladding layer was found to have a refractive index of 1.40 at a wavelength of 1.55 µm.

Then, 100 g of the polymer obtained in Synthesis Example 11 and 12 g of CYMEL 303 were dissolved in 250 g of methyl isobutyl ketone. The resulting solution was applied to the lower cladding layer by spin coating to form a film having a thickness of about 10 µm. This film was subjected to natural drying and then to a heat treatment at 150° C. for 30 min, thereby forming a core layer. This core layer was found to have a refractive index of 1.44 at a wavelength of 1.55 µm.

Then, the core layer was formed with a photoresist, followed by exposure to light through mask to form a photoresist pattern. Then, the core layer was subjected to dry etching to obtain a core ridge having a Y-branched waveguide pattern. Then, the above solution used for forming the lower cladding layer was applied the core ridge, followed by the same curing procedures as above, thereby forming an optical waveguide. This optical waveguide was cut into a test piece (widths: 5 cm) using a dicing saw. This test piece was measured for insertion loss. The results were not greater than 0.5 dB at a wavelength of 1.3 µm and not greater than 1.5 dB at 1.55 µm. Furthermore, polarization dependency of insertion loss was not greater than 0.1 dB even at 1.3 µm. Still furthermore, the test piece was found to have no substantial loss even under a high temperature of 180° C., showing a sufficient heat resistance.

Furthermore, it was possible to produce basic optical circuits such as directional coupler, star coupler, optical waveguide type grating ring resonator, and M×N multiplexing and branching. It was also possible to produce various POF waveguide elements, star coupler and Y branching.

Examples 7-11

In these examples respectively, the polymers obtained in Synthesis Examples 1, 10, 13, 16 and 17 were dissolved in propylene glycol monomethyl acetate to have a solid matter concentration of 10%. Then, triphenylsulfonium triflate made by Midori Kagaku Co., Ltd. was dissolved in an amount of 2 parts by weight per 100 parts by weight of each polymer, thereby preparing resist solutions of Examples 7-11. These resist solutions were applied to substrates by spin coating. The resulting resist films were found to have light transmittances of 68%, 56%, 52%, 60%, and 49% in Examples 7-11 respectively at a wavelength of 157 nm and at a film thickness of 100 nm, showing high transparency in vacuum ultraviolet wavelength region.

Then, the above resist solutions were filtered with a membrane filer (pore diameter: 0.2 micrometers). The resulting resist solutions were applied to silicon wafers by spin coating to form resist films each having a thickness of 250 nm. Then, the resist films were subjected to a preliminary baking at 110° C. for 60 seconds, followed by exposure at 248 nm using a KrF eximer laser micro scanner and then by a post exposure baking at 120° C. for 60 seconds. Then, the resist films were developed by a paddle method at 23° C. for 1 minute using 2.38 wt % tetramethylammonium hydroxide aqueous solution, followed by washing with pure water and then drying, thereby forming resist patterns. The resist patterns according to Examples 7-11 were respectively 23 mJ/cm, 14 mJ/cm, 17 mJ/cm, 12 mJ/cm, and 21 mJ/cm. Each resist pattern had lines and spaces with a resolution of 220 nm, a good pattern, and almost no development defects.

The entire contents of Japanese Patent Application No. 2001-222530 filed on Jul. 24, 2001, of which priority is claimed in the present application, are incorporated herein by reference.

What is claimed is:

1. A polymer prepared by polymerizing a polymerizable monomer represented by the formula (1), $$\text{(1)}$$

wherein
- $R^1$ is a hydrogen atom, a halogen atom, a hydrocarbon group or a fluorine-containing alkyl group;
- $R^2$ is an alkyl group that has a carbon atom number of at least three and that is optionally branched;
- $R^3$ is a hydrogen atom, a hydrocarbon group that is optionally branched, a fluorine-containing alkyl group, or a cyclic group having an aromatic or alicyclic structure, said $R^3$ optionally containing an oxygen atom or carbonyl group; and
- n is an integer of 1-2.

2. A polymer according to claim 1, wherein $R^1$ is a hydrogen atom, methyl group, trifluoromethyl group, or nonafluoro-n-butyl group.

3. A polymer according to claim 1, wherein $R^1$ is a methyl group.

4. A polymer according to claim 1, wherein $R^3$ is a hydrogen atom.

5. A polymer according to claim 1, wherein $R^1$ is a methyl group, and $R^3$ is a hydrogen atom.

6. A polymer according to claim 1, which is prepared by polymerizing the polymerizable monomer with another comonomer.

7. A polymer according to claim 6, wherein the another comonomer is at least one selected from the group consisting of olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

8. A polymer according to claim 1, which has a number average molecular weight of from 1,000 to 100,000.

9. A polymer prepared by polymerizing a polymerizable monomer represented by the formula (1), $$\text{(1)}$$

wherein
- $R^1$ is a halogen atom;
- $R^2$ is an alkyl group that has a carbon atom number of at least three and that is optionally branched;
- $R^3$ is a hydrogen atom, a hydrocarbon group that is optionally branched, a fluorine-containing alkyl group, or a cyclic group having an aromatic or alicyclic structure, said $R^3$ optionally containing an oxygen atom or carbonyl group; and
- n is an integer of 1-2.

10. A polymer according to claim 9, wherein $R^3$ is a hydrogen atom.

11. A polymer according to claim 9, which is prepared by polymerizing the polymerizable monomer with another comonomer.

12. A polymer according to claim 11, wherein the another comonomer is at least one selected from the group consisting of olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

13. A polymer according to claim 9, which has a number average molecular weight of from 1,000 to 100,000.

14. A polymer prepared by polymerizing a polymerizable monomer represented by the formula (1), $$\text{(1)}$$

wherein
- $R^1$ is a hydrogen atom, a halogen atom, a hydrocarbon group or a fluorine-containing alkyl group;
- $R^2$ is an alkyl group that has a carbon atom number of at least three and that is optionally branched;
- $R^3$ is a hydrocarbon group that is optionally branched, a fluorine-containing alkyl group, or a cyclic group having an aromatic or alicyclic structure, said $R^3$ optionally containing an oxygen atom or carbonyl group; and
- n is an integer of 1-2.

15. A polymer according to claim 14, wherein $R^1$ is a hydrogen atom, methyl group, trifluoromethyl group, or nonafluoro-n-butyl group.

16. A polymer according to claim 14, wherein $R^1$ is a methyl group.

17. A polymer according to claim 14, which is prepared by polymerizing the polymerizable monomer with another comonomer.

18. A polymer according to claim 17, wherein the another comonomer is at least one selected from the group consisting of olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

19. A polymer according to claim 14, which has a number average molecular weight of from 1,000 to 100,000.

20. A reflection preventive material, optical device material or resist material comprising a polymer prepared by polymerizing a polymerizable monomer represented by the formula (1),

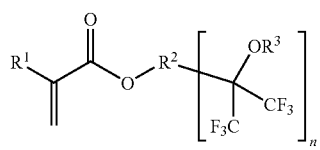

(1)

wherein
$R^1$ is a hydrogen atom, a halogen atom, a hydrocarbon group or a fluorine-containing alkyl group;
$R^2$ is an alkyl group that has a carbon atom number of at least three and that is optionally branched;
$R^3$ is a hydrogen atom, a hydrocarbon group that is optionally branched, a fluorine-containing alkyl group, or a cyclic group having an aromatic or alicyclic structure, said $R^3$ optionally containing an oxygen atom or carbonyl group; and
n is an integer of 1-2.

21. A material according to claim 20, wherein $R^1$ is a hydrogen atom, methyl group, trifluoromethyl group, or nonafluoro-n-butyl group.

22. A material according to claim 20, wherein $R^1$ is a methyl group.

23. A material according to claim 20, wherein $R^3$ is a hydrogen atom.

24. A material according to claim 20, wherein $R^1$ is a methyl group, and $R^3$ is a hydrogen atom.

25. A material according to claim 20, wherein the polymer is prepared by polymerizing the polymerizable monomer with another comonomer.

26. A material according to claim 25, wherein the another comonomer is at least one selected from the group consisting of olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

27. A material according to claim 20, wherein the polymer has a number average molecular weight of from 1,000 to 100,000.

28. A reflection preventive material, optical device material or resist material comprising a polymer prepared by polymerizing a polymerizable monomer represented by the formula (1),

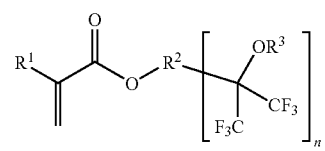

(1)

wherein
$R^1$ is a halogen atom;
$R^2$ is an alkyl group that has a carbon atom number of at least three and that is optionally branched;
$R^3$ is a hydrogen atom, a hydrocarbon group that is optionally branched, a fluorine-containing alkyl group, or a cyclic group having an aromatic or alicyclic structure, said $R^3$ optionally containing an oxygen atom or carbonyl group; and
n is an integer of 1-2.

29. A material according to claim 28, wherein $R^3$ is a hydrogen atom.

30. A material according to claim 28, wherein the polymer is prepared by polymerizing the polymerizable monomer with another comonomer.

31. A material according to claim 30, wherein the another comonomer is at least one selected from the group consisting of olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

32. A material according to claim 28, wherein the polymer has a number average molecular weight of from 1,000 to 100,000.

33. A material according to claim 28, which is a resist material.

34. A reflection preventive material, optical device material or resist material comprising a polymer prepared by polymerizing a polymerizable monomer represented by the formula (1),

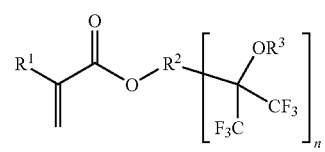

(1)

wherein
$R^1$ is a hydrogen atom, a halogen atom, a hydrocarbon group or a fluorine-containing alkyl group;
$R^2$ is an alkyl group that has a carbon atom number of at least three and that is optionally branched;
$R^3$ is a hydrocarbon group that is optionally branched, a fluorine-containing alkyl group, or a cyclic group having an aromatic or alicyclic structure, said $R^3$ optionally containing an oxygen atom or carbonyl group; and
n is an integer of 1-2.

35. A material according to claim 34, wherein $R^1$ is a hydrogen atom, methyl group, trifluoromethyl group, or nonafluoro-n-butyl group.

36. A material according to claim 34, wherein $R^1$ is a methyl group.

37. A material according to claim 34, wherein the polymer is prepared by polymerizing the polymerizable monomer with another comonomer.

38. A material according to claim 37, wherein the another comonomer is at least one selected from the group consisting of olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

39. A material according to claim 34, wherein the polymer has a number average molecular weight of from 1,000 to 100,000.

40. A material according to claim 34, which is a resist material.

* * * * *